United States Patent [19]

Westrup

[11] Patent Number: 4,543,336
[45] Date of Patent: Sep. 24, 1985

[54] INDICATOR FOR DETERMINING SULFUR DIOXIDE

[75] Inventor: Bernhard Westrup, Lubeck, Fed. Rep. of Germany

[73] Assignee: Drägerwerk Aktiengesellschaft, Fed. Rep. of Germany

[21] Appl. No.: 448,193

[22] Filed: Dec. 9, 1982

[30] Foreign Application Priority Data

Dec. 2, 1982 [DE] Fed. Rep. of Germany ....... 3204938

[51] Int. Cl.$^4$ .................... G01N 31/22; G01N 33/52
[52] U.S. Cl. .................... 436/122; 252/408.1
[58] Field of Search ............ 436/122, 10–19; 252/408.1

[56] References Cited

U.S. PATENT DOCUMENTS

| | | | |
|---|---|---|---|
| 2,736,638 | 2/1956 | McConnaughey | 23/232 |
| 3,539,450 | 11/1970 | Deutsch | 195/68 |
| 3,546,131 | 12/1970 | Stern | 252/408.1 |
| 3,607,695 | 10/1971 | Schneider | 204/180 S |
| 3,663,175 | 5/1972 | Depositar | 23/230 B |
| 3,874,852 | 4/1975 | Hamill | 23/230 B |
| 3,964,865 | 6/1976 | Das | 23/230 B |
| 4,042,329 | 8/1977 | Hochstrasser | 23/230 B |
| 4,115,067 | 9/1978 | Lyshkow | 436/122 X |
| 4,147,514 | 4/1979 | Magers et al. | 23/230 B |
| 4,372,874 | 2/1983 | Modrovich | 436/176 |

OTHER PUBLICATIONS

Analyst., vol. 85, (1960), pp. 147–148, "Notes".
Dixon, et al., "A Field Method . . . ", Analyst, vol. 83, (1958), pp. 199–202.

Primary Examiner—Edward A. Miller
Assistant Examiner—Catherine S. Kilby
Attorney, Agent, or Firm—McGlew and Tuttle

[57] ABSTRACT

An indicator for determining sulfur dioxide is required for monitoring, e.g. the content of the noxious substance in the air, due to emissions or in particularly jeopardized working places. With a high sensitivity and spacificity, it must allow simple handling and be ready to use immediately even after prolonged storage. Suitable for this purpose is the color reaction of nitroprussiate, which only takes place in the moist state. In order to attain a sufficient sensitivity an additive is principally required. Usual additives, however, lead on storage in the moist state to rapid decomposition so that immediate use is not possible after prolonged storage. This can be remedied by the use of a tetra-substituted ammonium salt as an additive, which yields at the same time a good sensitivity and storability in the moist state for months. It is preferably used in the form of the known test papers of test tapes.

10 Claims, No Drawings

1

INDICATOR FOR DETERMINING SULFUR DIOXIDE

FIELD AND BACKGROUND OF THE INVENTION

This invention relates in general to chemical indicating devices and in particular to a new and useful device for determining the presence of sulfur dioxide.

Sulfur dioxide is a noxious substance which appears increasingly with the expansion of technology. The increasingly required monitoring demands simple to use and reliable measuring means.

A known indicator for determining sulfur dioxide in air uses the specific color reaction of moist zinc nitroprussiate or nitroprusside on a carrier of filter paper. The air is sucked through this indicator, and the resulting discoloration is evaluated with a color standard. The indicator is known in two types with different use. In the first type, the filter paper is impregnated with a solution of zinc nitroprussiate in ammonia solution and dried. Immediately before use, this indicator must be moistened by spraying with water so that it cannot react immediately. In the second type, the impregnation of the filter paper is effected with a solution of zinc nitroprussiate and solid ammonium acetate and adding glycerin. The hygroscopic action of glycerin makes moistening of the indicator before use unnecessary. The addition of ammonium acetate also ensures a good sensitivity. The stability of this indicator is very limited, however, since the reagent decomposes after a storage time of about 4 weeks (Analyst. vol. 85 (1960), S.147–148). A known indicator for determining sulfur dioxide in the atmosphere contains on paper or polymer film pararosaniline with a hygroscopic substance in gelatin or polyvinyl alcohol. In use, the indicator is exposed for a certain time to the environment to be monitored and the discoloration is evaluated according to a comparison method. Unsatisfactory is the crosssensitivity to nitrous gases, which is frequently found in emission controls together with sulfur dioxide (British Pat. No. 1,498,192).

SUMMARY OF THE INVENTION

The invention provides an indicator for determining sulfur dioxide which shows good stability with a high sensitivity and specificity, as well as immediate readiness with simple handling.

In accordance with the invention a nitroprussiate or nitroprusside plus a hygroscopic substance and an addition of a tetra-substituted ammonium salt is provided as indicator for determining sulfur dioxide.

Accordingly, an object of the invention is to provide an indicator which will determine sulfur dioxide which has a good stability with a high sensitivity and specificity and may be employed immediately without elaborate preparation.

GENERAL DESCRIPTION OF THE PREFERRED EMBODIMENT

The addition of the tetra-substituted ammonium salt has the effect, similar to other known additives, of causing a high sensitivity. In contrast to the known additives, however, there is no side effect in the form of a decomposition in the ready to use moist state, so that the stability is very good when used immediately. This effect of the tetra-substituted ammonium salt is surprising, since it is generally known as a phase transfer catalyst.

Suitable as nitroprussiate is preferably zinc nitroprussiate, but also nickel-, cobalt-, cadmium-, or copper nitroprussiate. As conventional carriers, hygroscopic substances can be used with proven possibilities of application.

For use, the indicator is kept in storage and merely has to be exposed in a known device to the air to be tested, and the resulting discoloration is evaluated, so that the handling is very simple.

With the invention it is also possible to determine sulfur dioxide which instead of the addition which is employed, a substance which is more available on the market may be employed such as one having alkyl or aryl radicals. These specific forms of tetra-substituted ammonium salts i.e. N,N,N,N-tetraalkyl and/or aryl-substituted ammonium salts, permit an adaption of the manufacture to the changing demand of the substances in the market. Some of the proven carriers which may be employed for the detector is a paper or a plastic film or a silica gel.

In one embodiment of the invention, the indicator consists of zinc acetate, sodium nitroprussiate and tetramethylammonium acetate, i.e. N,N,N,N-tetramethylammonium acetate, as well as glycerin for stabilizing the moisture on a filter paper. This indicator can be stored at room temperature for months in the dark without any substantial loss of sensitivity. Its sensitivity suffices to make measurements in the ppm range within seconds (MAK-monitoring). By extending the exposition time to several minutes, measurements in the ppb-range (emmission) are also possible.

While a specific embodiment of the invention has been shown and described in detail to illustrate the application of the principles of the invention, it will be understood that the invention may be embodied otherwise without departing from such principles.

What is claimed is:

1. Indicator for determining the presence of sulfur dioxide, comprising a nitroprusside, a hygroscopic substance, and an addition of an N,N,N,N-tetra-substituted ammonium salt for providing high sensitivity and simultaneously stability against moisture for the indicator, the N-substituents of the ammonium salt being selected from the group consisting of alkyl and aryl radicals.

2. Indicator of claim 1 wherein said N-substituents comprise alkyl radicals.

3. Indicator of claim 1 wherein said N-substituents comprise aryl radicals.

4. Indicator of claim 1 wherein said N-substituents comprise alkyl and aryl radicals.

5. Indicator of claim 1 including a carrier comprising paper.

6. Indicator of claim 1 including a carrier comprising a plastic film.

7. Indicator of claim 1 including a carrier comprising a silica gel.

8. Indicator for determining the presence of sulfur dioxide, comprising a nitroprusside, a hygroscopic substance, and an addition of an N,N,N,N-tetramethyl-ammonium salt.

9. Indicator of claim 8 wherein said salt is N,N,N,N-tetramethyl-ammonium acetate.

10. Indicator of claim 8 including a carrier.

* * * * *